United States Patent
Hanlon et al.

(10) Patent No.: US 8,947,654 B2
(45) Date of Patent: *Feb. 3, 2015

(54) FLOW CELL ASSEMBLY FOR LIQUID SAMPLE ANALYZER

(71) Applicant: PerkinElmer Health Sciences, Inc., Waltham, MA (US)

(72) Inventors: Gregory Hanlon, Windsor, CT (US); Timothy Neal, Harwinton, CT (US); Richard Edwards, Brookfield, CT (US); Joseph L. DiCesare, Redding, CT (US); David M. Aikens, Chester, CT (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 0 days.
This patent is subject to a terminal disclaimer.

(21) Appl. No.: 14/281,351

(22) Filed: May 19, 2014

(65) Prior Publication Data
US 2014/0253916 A1 Sep. 11, 2014

Related U.S. Application Data

(63) Continuation of application No. 13/780,984, filed on Feb. 28, 2013.
(60) Provisional application No. 61/762,570, filed on Feb. 8, 2013, provisional application No. 61/713,405, filed on Oct. 12, 2012.

(51) Int. Cl.
*G01N 33/36* (2006.01)
*G01N 21/05* (2006.01)
(Continued)

(52) U.S. Cl.
CPC ............ *G01N 21/05* (2013.01); *G01N 21/0303* (2013.01); *G01N 21/255* (2013.01); *G01N 2030/746* (2013.01); *G01N 21/03* (2013.01)
USPC ........................................................ 356/246

(58) Field of Classification Search
CPC ... G01N 21/05; G01N 21/03; G01N 21/0303; G01N 30/74; G01N 21/031
USPC ........................................................ 356/246
See application file for complete search history.

(56) References Cited

U.S. PATENT DOCUMENTS 4,571,078 A 2/1986 Capps, II
5,140,169 A 8/1992 Evens et al.
(Continued)

FOREIGN PATENT DOCUMENTS

EP 2 124 036 A1 11/2009
GB 2 486 641 A 6/2012
WO WO 2012/055432 A1 5/2012

OTHER PUBLICATIONS

Starna® Flow Cells for Spectophotometers, Retrieved Aug. 3, 2012 from URL http://www.starna.com/ukhome/d_cells/d_cells_s/flow/xflow.html, 3 pages.
(Continued)

*Primary Examiner* — Tarifur Chowdhury
*Assistant Examiner* — MD Rahman
(74) *Attorney, Agent, or Firm* — Myers Bigel Sibley & Sajovec, PA

(57) ABSTRACT

A flow cell assembly for use in a liquid sample analyzer including a radiation source, a sensing device and a liquid sample source to supply a liquid sample includes an entrance joint member, a liquid core waveguide, a liquid sample feed tube, and an input optical fiber. The entrance joint member includes a waveguide receiving bore and a feed tube receiving bore. The liquid core waveguide is mounted in the waveguide receiving bore and defines a waveguide bore. The liquid sample feed tube is mounted in the feed tube receiving bore such that the liquid sample feed tube is in fluid communication with the waveguide bore to fluidly connect the liquid sample source to the waveguide bore. The input optical fiber is mounted in the entrance joint member to transmit radiation from the radiation source to the waveguide bore, which radiation is transmitted through the waveguide bore and the liquid sample therein to the sensing device.

23 Claims, 15 Drawing Sheets

(51) Int. Cl.
*G01N 21/03* (2006.01)
*G01N 21/25* (2006.01)
*G01N 30/74* (2006.01)

(56) References Cited

U.S. PATENT DOCUMENTS

| | | |
|---|---|---|
| 5,153,679 A | 10/1992 | Gilby |
| 5,184,192 A | 2/1993 | Gilby et al. |
| 5,416,879 A | 5/1995 | Liu |
| 5,444,807 A | 8/1995 | Liu |
| 5,608,517 A | 3/1997 | Munk |
| 6,188,813 B1 | 2/2001 | Dourdeville et al. |
| 6,314,227 B1 | 11/2001 | Nath |
| 6,526,188 B2 | 2/2003 | Dourdeville et al. |
| 6,542,231 B1 | 4/2003 | Garrett |
| 6,678,051 B2 | 1/2004 | Gerner et al. |
| 6,734,961 B2 | 5/2004 | Gerner et al. |
| 7,005,090 B2 | 2/2006 | Mueller et al. |
| 7,259,840 B1 | 8/2007 | Gerner et al. |
| 7,298,472 B2 | 11/2007 | Gerner et al. |
| 7,362,429 B2 | 4/2008 | Gilby |
| 7,808,619 B2 | 10/2010 | Gerner et al. |
| 7,847,944 B2 | 12/2010 | Buettner et al. |
| 7,859,657 B2 | 12/2010 | Jeannotte et al. |
| 7,914,852 B2 | 3/2011 | Belz et al. |
| 2001/0010747 A1 | 8/2001 | Dourdeville et al. |
| 2002/0071123 A1 | 6/2002 | Miller et al. |
| 2009/0009758 A1 | 1/2009 | Gilby |

OTHER PUBLICATIONS

International Search Report and Written Opinion issued in corresponding PCT Application No. PCT/US2013/063909, mailed Jan. 22, 2014 (12 pages).

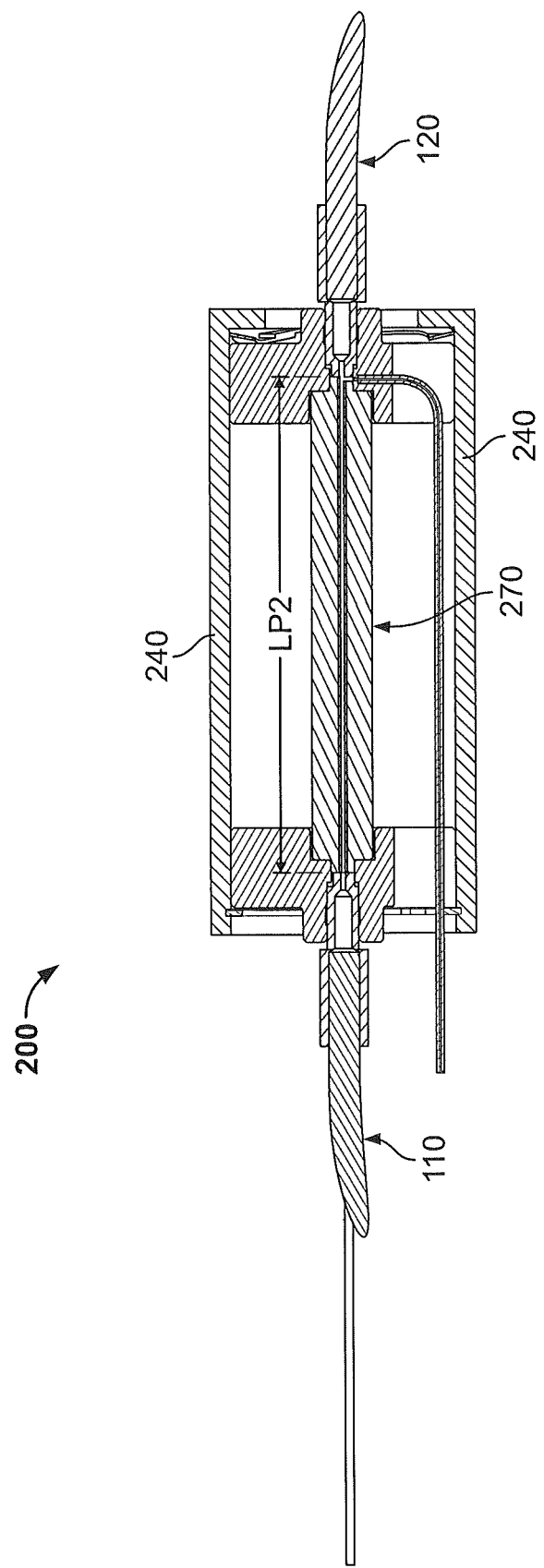

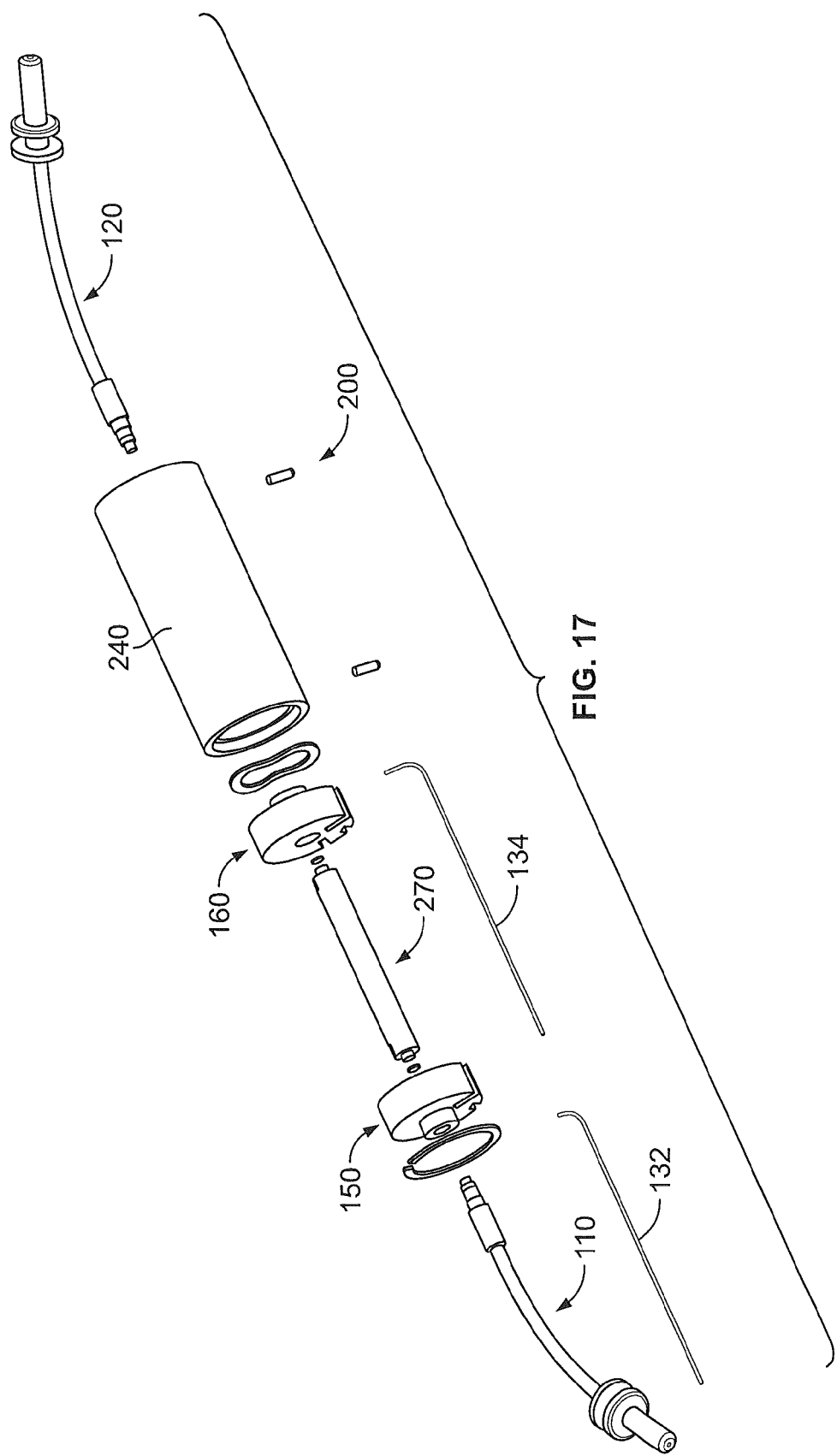

FLOW CELL ASSEMBLY FOR LIQUID SAMPLE ANALYZER

RELATED APPLICATION(S)

The present application is a continuation application claiming priority from U.S. patent application Ser. No. 13/780,984, filed Feb. 28, 2013, which claims the benefit of and priority from U.S. Provisional Patent Application No. 61/762,570, filed Feb. 8, 2013, and U.S. Provisional Patent Application Ser. No. 61/713,405, filed Oct. 12, 2012, the disclosures of which are incorporated herein by reference in their entireties.

FIELD

The present technology relates to liquid sample analyzers and flow cells therefor.

BACKGROUND

Liquid sample analyzers of known design include a flow cell, a light source for providing light to the flow cell, a liquid sample source for flowing a liquid sample through the flow cell, and a detector (e.g., a spectrometer) for receiving light from the flow cell (i.e., the light from the light source as modified by transmission through the flow of the liquid sample in the flow cell). In some instances, it is necessary to package the flow cell in a flow cell assembly providing light transmission and fluidic connections between the flow cell and the light source and the liquid sample source.

SUMMARY

According to embodiments of the present technology, a flow cell assembly for use in a liquid sample analyzer, the liquid sample analyzer including a radiation source, a sensing device and a liquid sample source to supply a liquid sample, includes a unitary entrance joint member, a liquid core waveguide, a liquid sample feed tube, and an input optical fiber. The entrance joint member includes a waveguide receiving bore and a feed tube receiving bore. The liquid core waveguide is mounted in the waveguide receiving bore. The liquid core waveguide defines a waveguide bore. The liquid sample feed tube is mounted in the feed tube receiving bore such that the liquid sample feed tube is in fluid communication with the waveguide bore to fluidly connect the liquid sample source to the waveguide bore. The input optical fiber is mounted in the entrance joint member to transmit radiation from the radiation source to the waveguide bore, which radiation is transmitted through the waveguide bore and the liquid sample therein to the sensing device.

According to some embodiments, the waveguide bore defines a longitudinally extending waveguide bore axis, and the feed tube receiving bore extends radially with respect to the waveguide bore axis.

In some embodiments, the feed tube receiving bore includes a feed tube engaging section and a counterbore section, the feed tube engaging section forms an interference fit with the liquid sample feed tube, and the flow cell assembly further includes an adhesive in the counterbore section bonding the liquid sample feed tube to the counterbore section.

The liquid core waveguide may include an outer waveguide body and a cladding layer. The outer waveguide body defines a waveguide body bore. The cladding layer is mounted in the waveguide body bore and defines the waveguide bore. The cladding layer is formed of a material having a lower refractive index than the liquid sample.

In some embodiments, the flow cell assembly includes: an exit joint member including a waveguide receiving bore and an exit tube receiving bore, wherein the liquid core waveguide is also mounted in the waveguide receiving bore of the exit joint member; a liquid sample exit tube mounted in the exit tube receiving bore such that the liquid sample exit tube is in fluid communication with the waveguide bore to fluidly connect the waveguide bore to a liquid sample receiver; and an output optical fiber mounted in the exit joint member to transmit radiation from the waveguide bore to the sensing device.

According to embodiments of the present technology, a flow cell assembly for use in a liquid sample analyzer, the liquid sample analyzer including a radiation source, a sensing device and a liquid sample source to supply a liquid sample, includes a liquid core waveguide, an input optical fiber, and a nonresilient mask member. The liquid core waveguide includes a cladding layer formed of a material having a lower refractive index than the liquid sample. The cladding layer defines: an axially extending waveguide bore to receive the liquid sample, the waveguide bore having a bore input end and a bore output end; and an input opening at the bore input end. The input optical fiber has an optical fiber end face mounted at the input opening to transmit radiation from the radiation source into the waveguide bore, which radiation is transmitted through the waveguide bore and the liquid sample therein to the sensing device. The nonresilient mask member is interposed between the optical fiber end face and the input opening. The mask member defines an aperture through which light is transmitted from the optical fiber end face into the waveguide bore. The mask member blocks light from the optical fiber end face not directed through the aperture.

In some embodiments, the mask member is formed of a material having a Young's Modulus of at least about 14,000 ksi. The mask member may be formed of metal.

According to some embodiments, the mask member has opposed inner and outer sides, the optical fiber end face directly engages the outer side, and an input end of the cladding layer directly engages the inner side.

In some embodiments, the flow cell assembly includes: an output opening defined in the cladding layer at the bore output end; an output optical fiber having an output optical fiber end face mounted at the output opening to transmit radiation from the waveguide bore to the sensing device; and a nonresilient second mask member interposed between the output optical fiber end face and the output opening, the second mask member defining an output aperture through which light is transmitted from the waveguide bore into the output optical fiber end face, wherein the second mask member blocks light not directed from the waveguide bore through the output aperture.

According to embodiments of the present technology, a flow cell assembly for use in a liquid sample analyzer, the liquid sample analyzer including a radiation source, a sensing device and a liquid sample source to supply a liquid sample, includes a joint member, a liquid core waveguide, and an optical fiber assembly. The joint member includes an axially extending alignment bore. The alignment bore includes a waveguide receiving bore section and an optical fiber termination receiving bore section. The liquid core waveguide is mounted in the waveguide receiving bore section, The liquid core waveguide defines a waveguide bore. The optical fiber assembly includes an optical fiber and an optical fiber termination mounted in the optical fiber termination receiving bore section. The optical fiber has an ex-posed optical fiber end face adjacent the optical fiber termination. The alignment bore radially aligns the liquid core waveguide with the optical fiber termination and thereby radially aligns the optical fiber end face with the waveguide bore. The optical fiber is operative to transmit radiation from the radiation source to the waveguide bore, which radiation is transmitted through the waveguide bore and the liquid sample therein to the sensing device.

In some embodiments, the alignment bore further includes an interface bore section axially interposed between the waveguide receiving bore section and the optical fiber termination receiving bore section, and an end portion of the liquid core waveguide and an opposing portion of the optical fiber termination are each disposed in the interface bore section. The flow cell assembly may include a mask member disposed in the interface bore section between the liquid core waveguide and the optical fiber termination, the mask member defining an aperture to permit transmission of light from the optical fiber end face through the aperture into the waveguide bore.

According to some embodiments, the liquid core waveguide is fluidly sealed in the alignment bore.

In some embodiments, the alignment bore coaxially aligns the optical fiber and the waveguide bore.

The optical fiber termination may be a ferrule.

According to embodiments of the present technology, a flow cell assembly for use in a liquid sample analyzer, the liquid sample analyzer including a radiation source, a sensing device and a liquid sample source to supply a liquid sample, includes a liquid core waveguide, and an input optical fiber. The liquid core waveguide includes a cladding layer formed of a material having a lower refractive index than the liquid sample. The cladding layer defines: an axially extending waveguide bore having a bore input end and a bore output end; an input opening at the bore input end; and a liquid sample feed slot extending radially through the cladding layer and intersecting each of the waveguide bore and the input opening. The flow cell assembly is configured to feed a flow of the liquid sample into the waveguide bore through the liquid sample feed slot. The input optical fiber is mounted at the input opening to transmit radiation from the radiation source into the waveguide bore, which radiation is transmitted through the waveguide bore and the liquid sample therein to the sensing device.

In some embodiments, the cladding layer defines an exit end opening at the output bore end, the cladding layer further defines a liquid sample exit slot extending radially through the cladding layer and intersecting each of the waveguide bore and the output opening, and the flow cell assembly is configured to remove the flow of the liquid sample from the waveguide bore through the liquid sample exit slot.

According to some embodiments, the cladding layer is a tubular sleeve terminating at the input and output bore ends and the waveguide bore has a substantially uniform diameter from the first bore end to the second bore end.

Further features, advantages and details of the present technology will be appreciated by those of ordinary skill in the art from a reading of the figures and the detailed description of the preferred embodiments that follow, such description being merely illustrative of the present technology.

BRIEF DESCRIPTION OF THE DRAWINGS

FIG. 16 is a fragmentary, cross-sectional view of a flow cell assembly according to further embodiments of the technology.

FIG. 17 is an exploded, perspective view of the flow cell assembly of FIG. 16.

DETAILED DESCRIPTION

Figure 1:
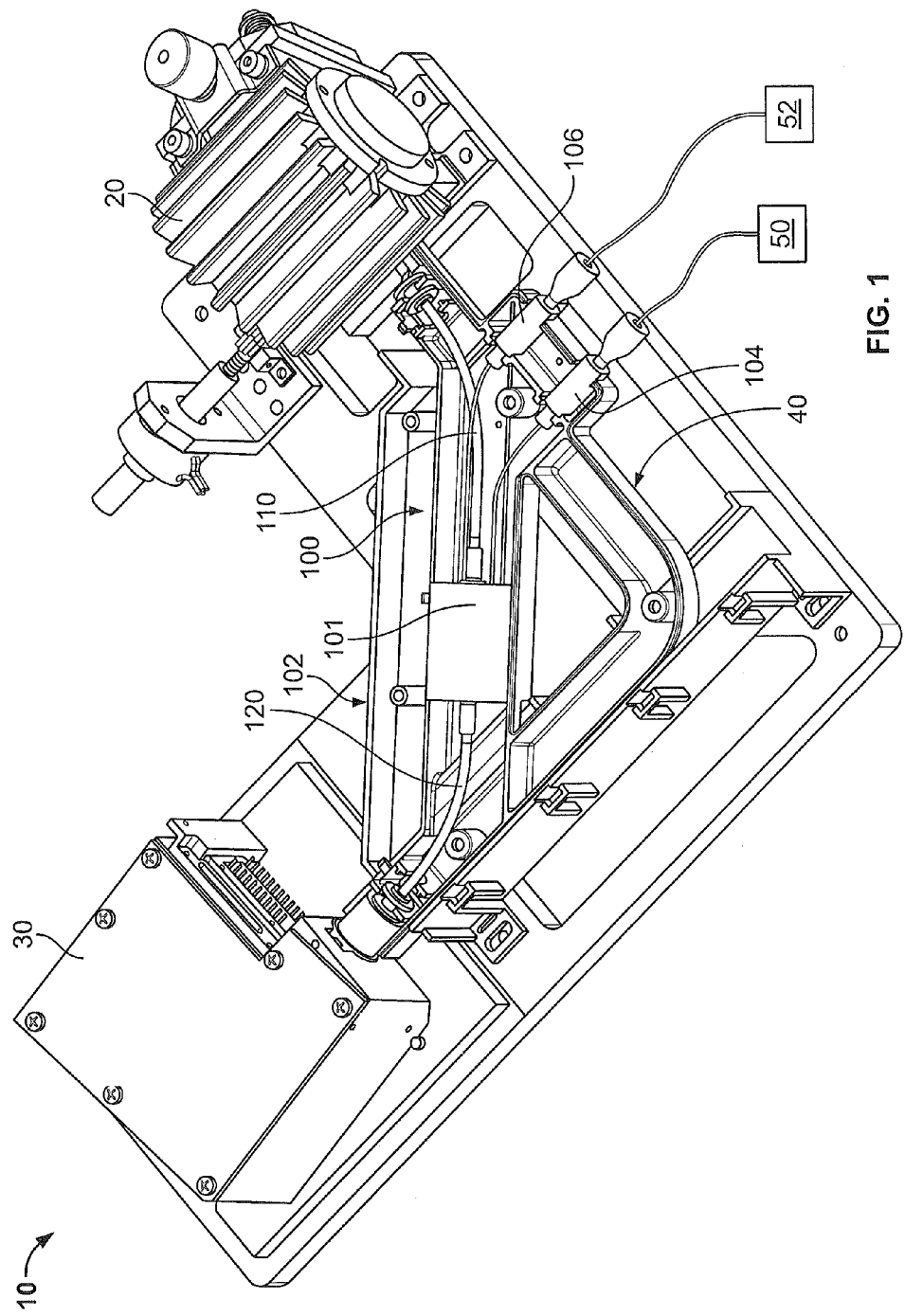
FIG. 1 is a perspective view of a liquid sample analyzer including a flow cell assembly according to embodiments of the technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this technology belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

As used herein, "monolithic" means an object that is a single, unitary piece formed or composed of a material without joints or seams.

Embodiments of the present technology are directed to flow cell assemblies for liquid sample analyzers. More particularly, flow cell assemblies as disclosed herein can be used in photometric apparatus for spectroscopic analysis, such as high performance chromatography (HPLC), capillary LC, and capillary electrophoresis (CE). In general, the disclosed flow cell assembly provides a flow-through liquid core waveguide having a waveguide bore through which a stream of a liquid sample is flowed. The flow cell assembly provides fluidics for introducing the liquid sample into and removing the liquid sample from the waveguide bore. The flow cell assembly also provides a source optical fiber to guide radiation (e.g., UV or visible light) from a radiation source to the waveguide and a detector optical fiber to guide the radiation from the waveguide to a sensing device. The light from the light source optical fiber is guided (from the source optical fiber to the detector optical fiber) through the waveguide and the liquid sample flowing therethrough by total internal reflection at the boundary between the liquid sample and the waveguide bore.

With reference to FIG. 1, a liquid sample analyzer 10 according to embodiments of the technology is shown therein. The liquid sample analyzer 10 includes a remote radiation or light source 20, a remote sensing device or detector 30, a flow cell module 40 (FIGS. 2-15), a remote liquid sample source 50, and a remote liquid sample receiver 52. The flow cell module 40 includes a flow cell assembly 100 according to embodiments of the technology.

The radiation source 20 can be any suitable source of radiation or light for enabling spectroscopic analysis. According to some embodiments, the source 20 is a deuterium lamp.

The sensing device 30 may be any suitable sensing device or detector for spectroscopic analysis. According to some embodiments, the detector 30 is a spectrometer including a photodiode array (PDA).

The liquid sample source 50 may be any suitable source including a supply of the sample to be analyzed in a liquid solvent. According to some embodiments, the solvent is aqueous. In some embodiments, the solvent is inorganic or a mixture of inorganic and aqueous. The liquid sample receiver 52 may be a waste receptacle or a down line process (such as a secondary detector). According to some embodiments, at least one of the liquid sample source 50 and the liquid sample receiver 52 is provided with a pump to generate a forced flow of the liquid sample through the flow cell assembly 100.

Figure 2:
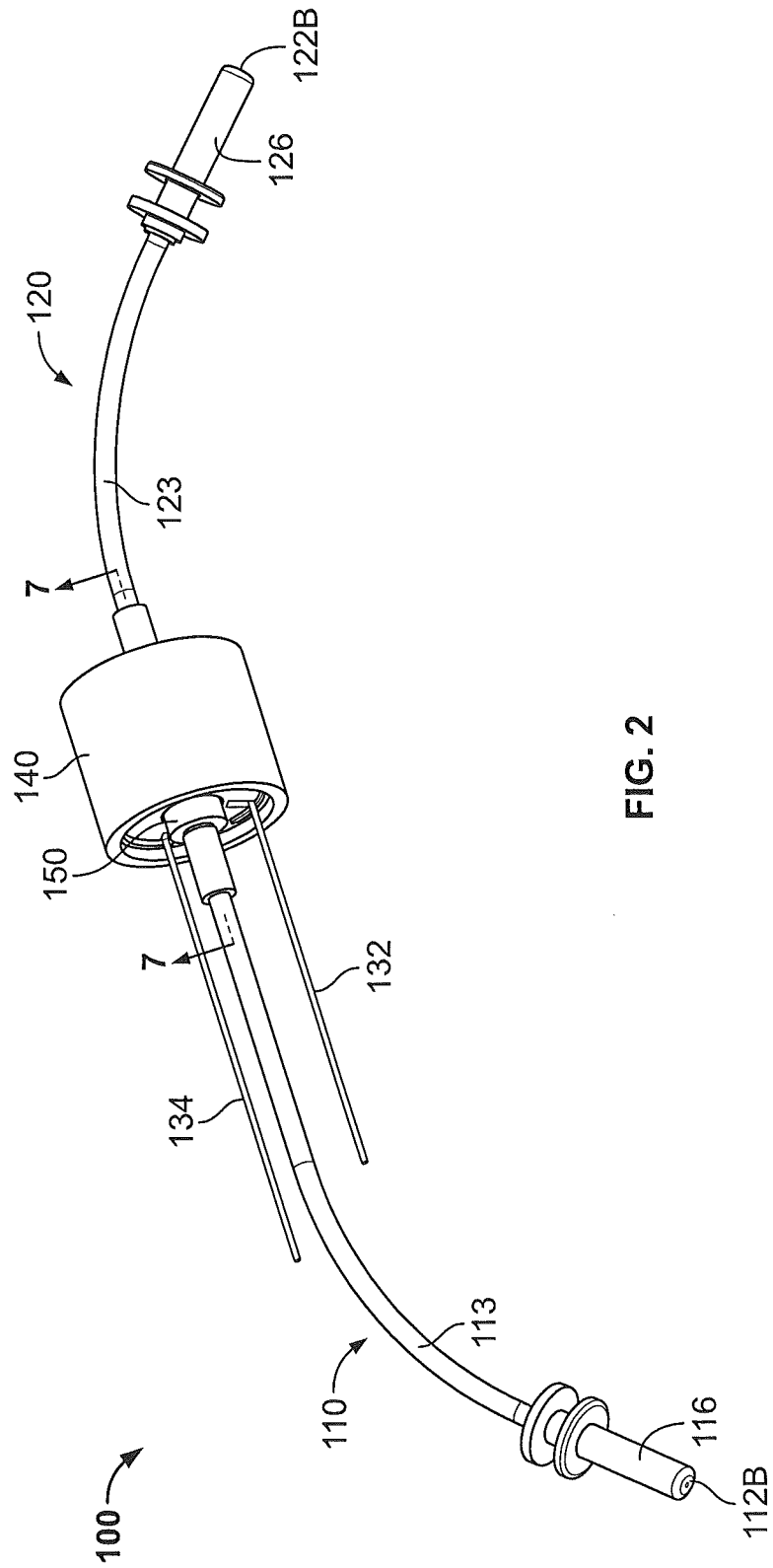
FIG. 2 is a front perspective view of the flow cell assembly of FIG. 1.
Figure 3:
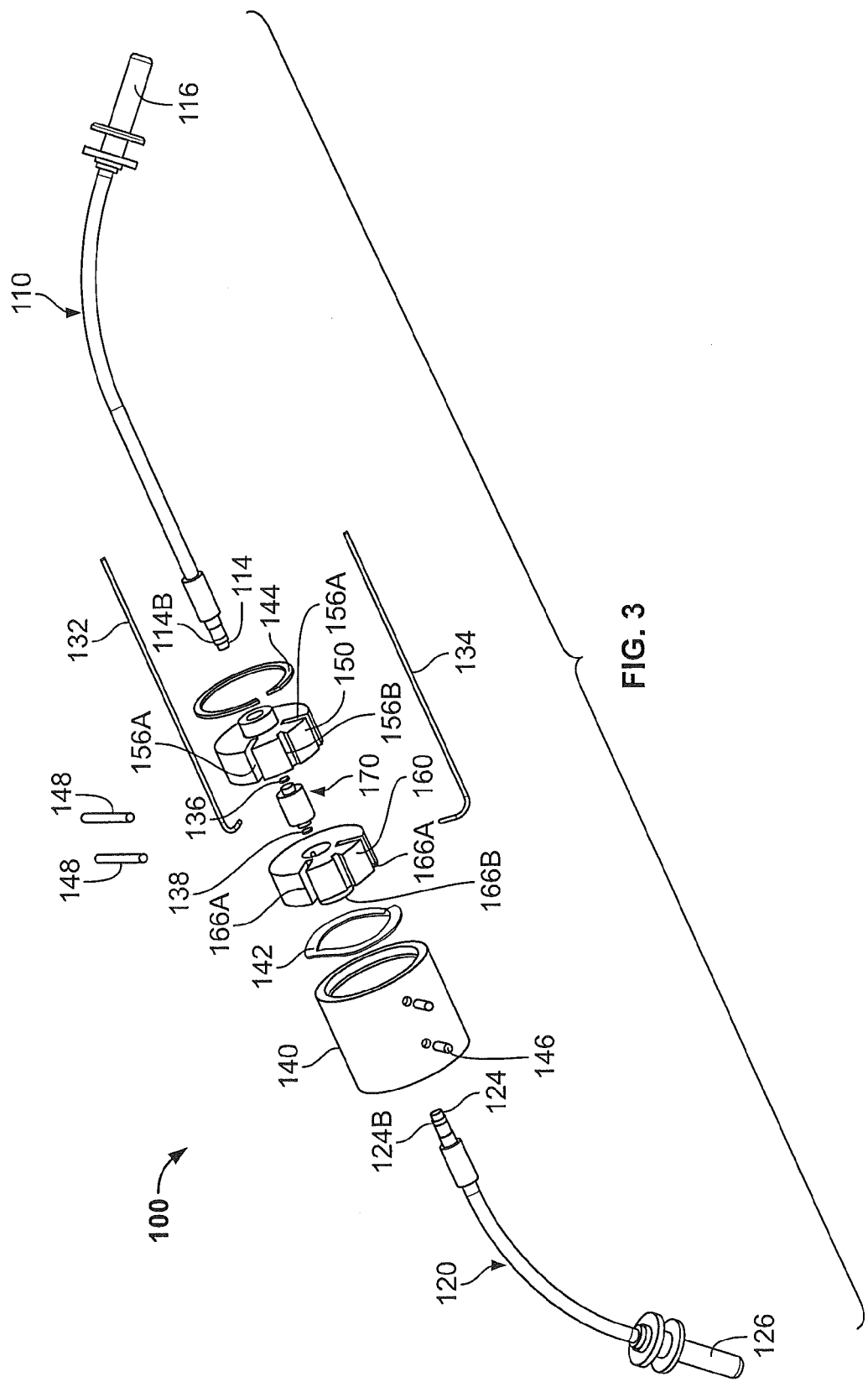
FIG. 3 is an exploded, perspective view of the flow cell assembly of FIG. 2.
Figure 4:
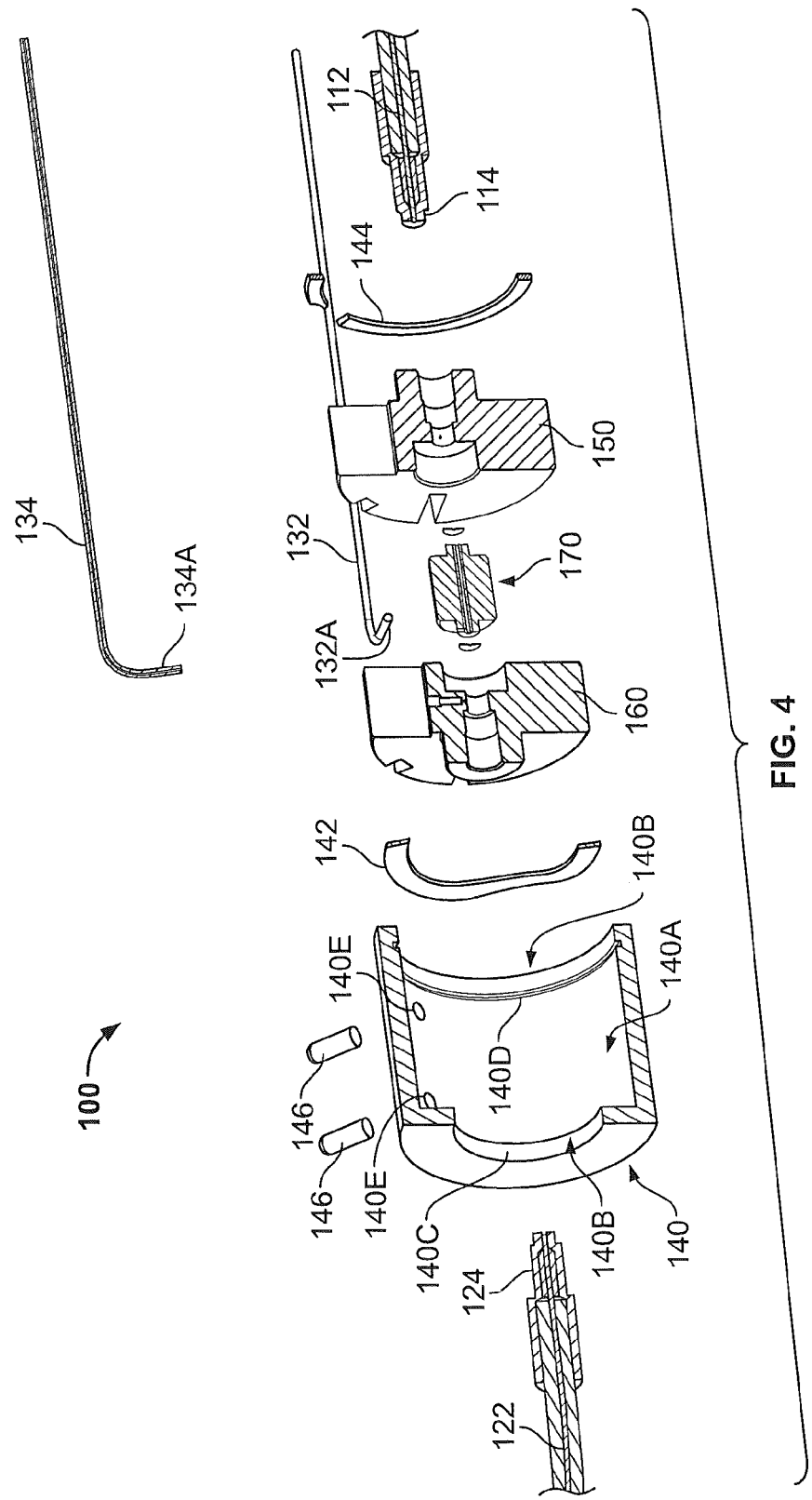
FIG. 4 is a fragmentary, exploded, cross-sectional, rear perspective view of the flow cell assembly of FIG. 2.

With reference to FIGS. 2-4, the flow cell assembly 100 includes a source connectorized optical fiber 110, a detector connectorized optical fiber 120, a feed capillary tube 132, an exit capillary tube 134, an entrance light mask member 136, an exit light mask member 138, an outer housing 140, a wave spring 142, a retainer clip 144, outer locator pins 146, inner locator pins 148, an input or entrance "T" member or joint member 150, an output or exit "T" member or joint member 160, and a waveguide 170. As shown, the foregoing components are assembled to form a modular device. The flow cell assembly 100 may be mounted in a housing or holder 102 (FIG. 1).

Figure 7:
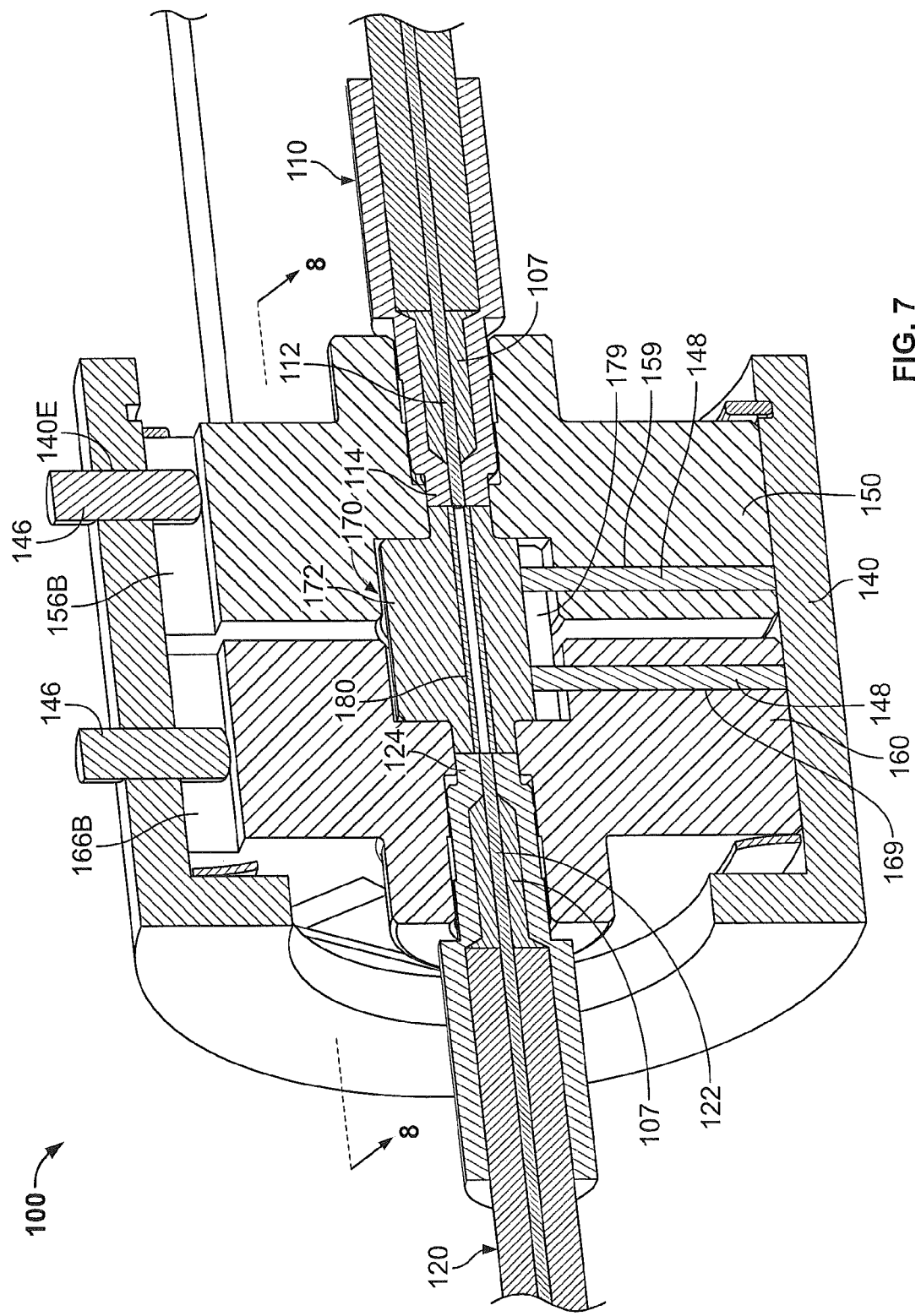
FIG. 7 is a fragmentary, cross-sectional, rear perspective view of the flow cell assembly of FIG. 2 taken along the line 7-7 of FIG. 2.
Figure 8:
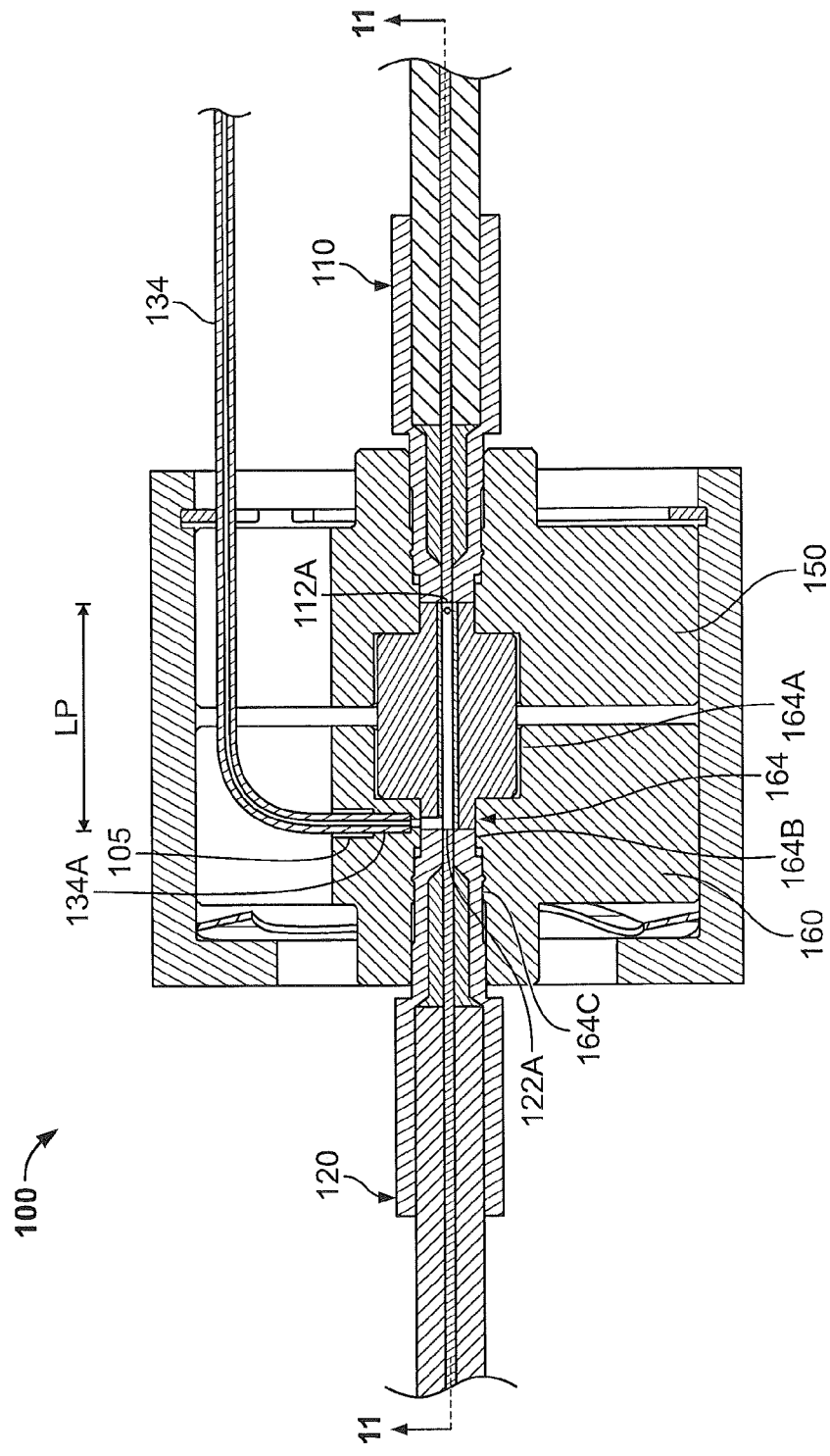
FIG. 8 is a fragmentary, cross-sectional view of the flow cell assembly of FIG. 2 taken along the line 8-8 of FIG. 7.

The source connectorized fiber 110 includes a flexible optical fiber or waveguide 112, a termination or ferrule 114, and an input connector or termination 116. The optical fiber 112 may be an optical fiber including a solid glass core and a solid glass cladding and may be covered in a protective jacket 113. The ferrule 114 is mounted on one end of the optical fiber 112 such that an output end face 112A (FIG. 12) is exposed adjacent and substantially flush with an end face 114A of the ferrule 114. The ferrule 114 may be secured to the optical fiber 112 by epoxy 107 or other adhesive (FIG. 7). The termination 116 is mounted on the opposite end of the optical fiber 112 such that an input end 112B (FIG. 2) of the optical fiber 112 is exposed. In use, the termination 116 is installed proximate the light source 20 such that light from the light source 20 is directed into the optical fiber 112 through the end face 112B and transmitted through the fiber 112 and out of the fiber 112 through the end face 112A. The ferrule 114 has an annular rib 114B (FIG. 9) on its outer diameter.

The detector connectorized fiber 120 includes a flexible optical fiber 122 (which may be covered in a protective jacket 123), a termination or ferrule 124, and an output connector or termination 126. The ferrule 124 is mounted on an end of the optical fiber 122 such that an input end face 122A (FIG. 9) is exposed adjacent and substantially flush with an input end face 124A (FIG. 2) of the ferrule 124. The ferrule 124 may be secured to the optical fiber 122 by epoxy 107 or other adhesive (FIG. 7). The termination 126 is mounted on the opposite end of the fiber 122 such that an output end 122B (FIG. 2) of the fiber 122 is exposed. In use, the termination 126 is mated with the detector 30 to transmit light from the end face 122A to the detector 30. For example, the termination 126 may be a fiber optic connector configured to operatively mate with a corresponding fiber optic connector of the detector 30. The ferrule 124 has an annular rib 124B (FIG. 12) on its outer diameter.

Figure 9:
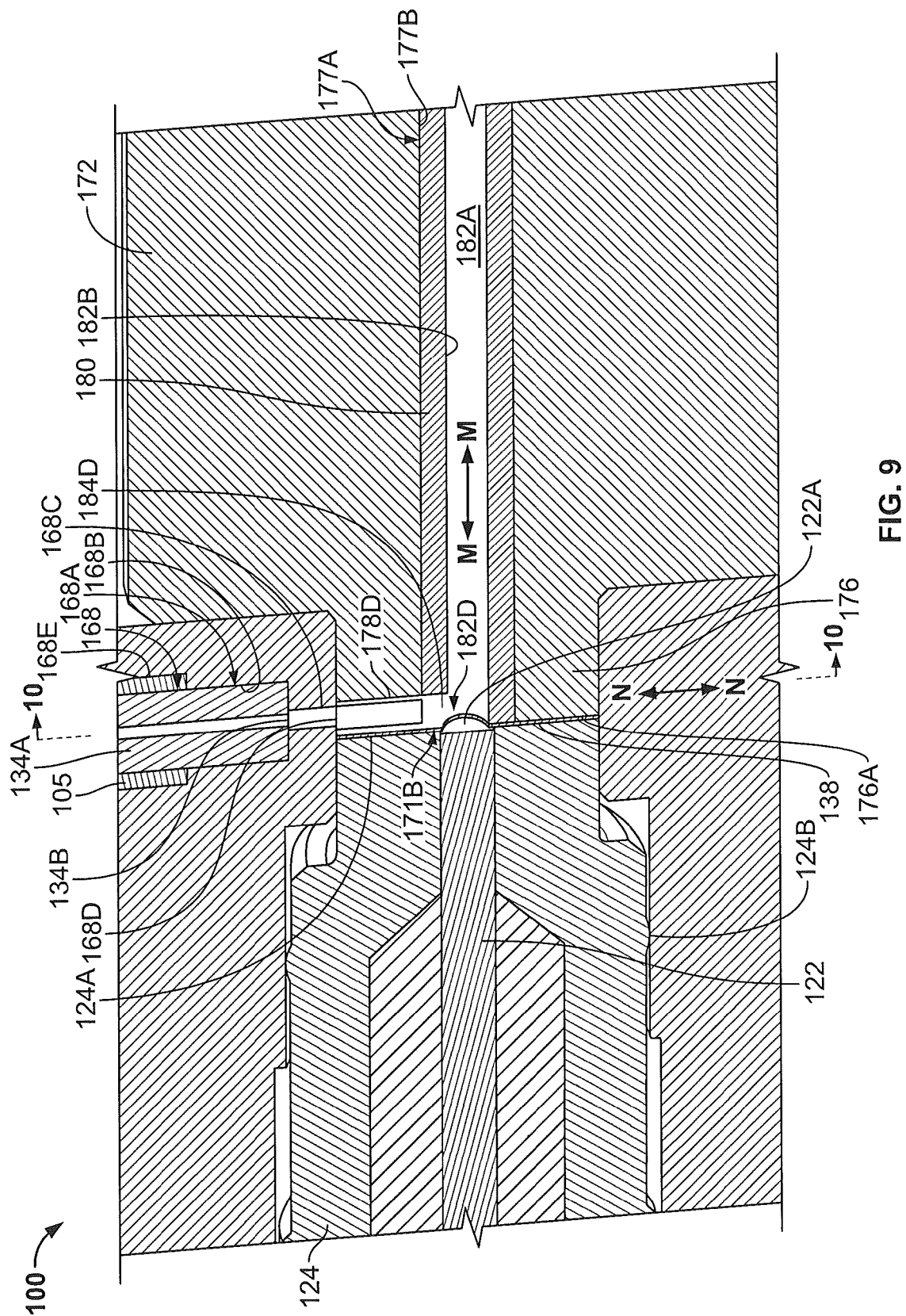
FIG. 9 is an enlarged, fragmentary, cross-sectional view of the flow cell assembly of FIG. 2 taken along the line 8-8 of FIG. 7.
Figure 10:
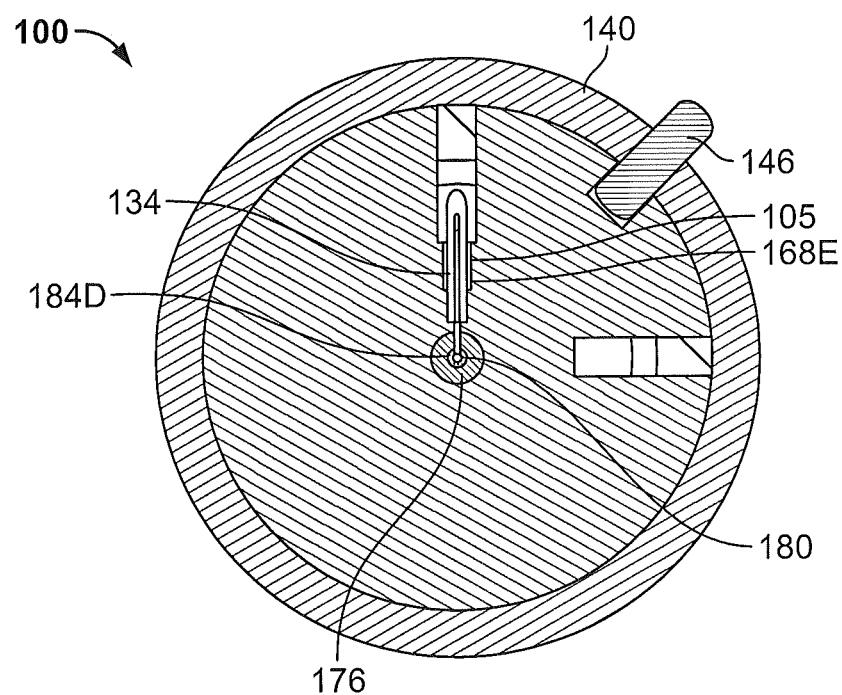
FIG. 10 is a cross-sectional view of the flow cell assembly of FIG. 2 taken along the line 10-10 of FIG. 9.
Figure 11:
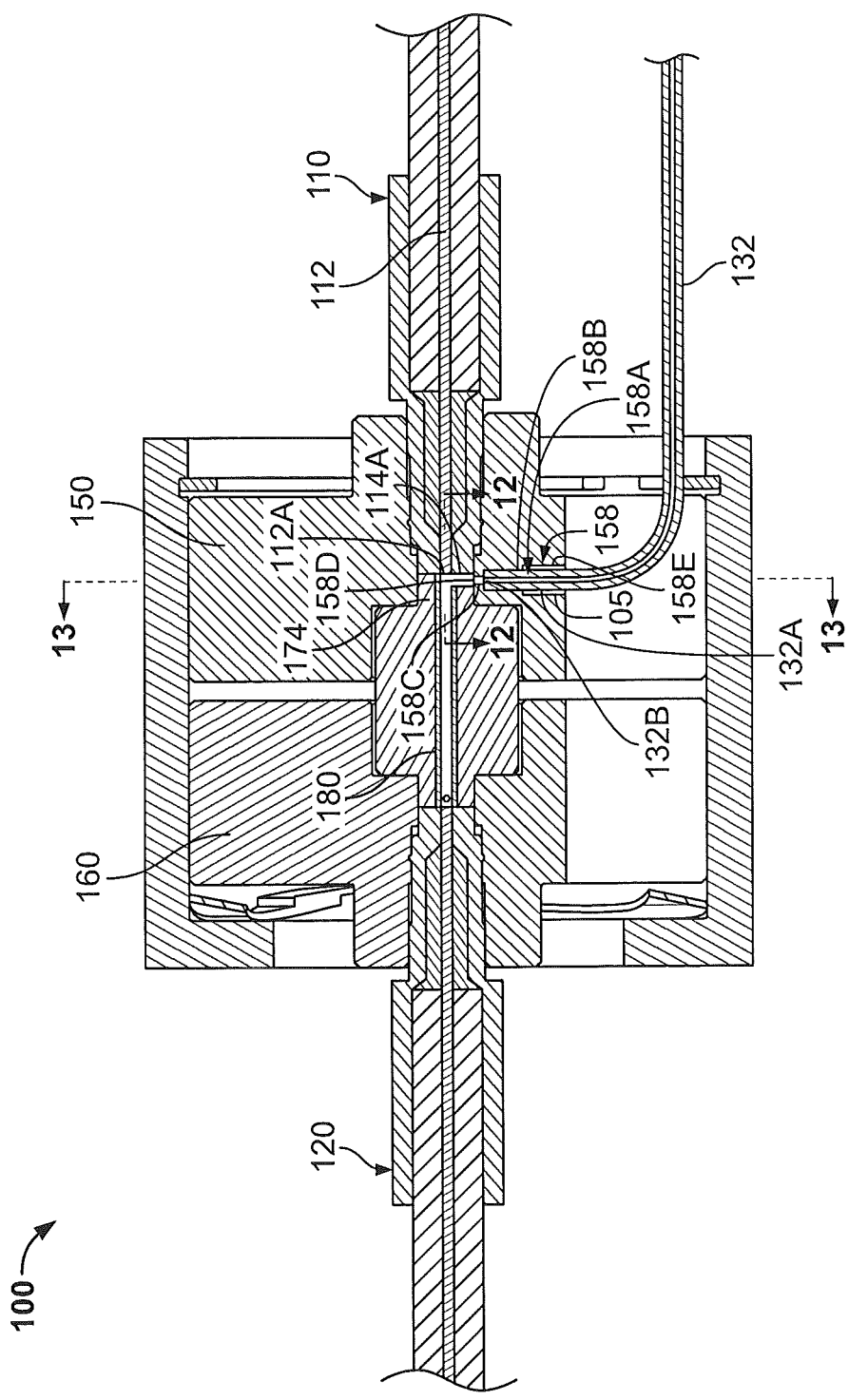
FIG. 11 is a cross-sectional view of the flow cell assembly of FIG. 2 taken along the line 11-11 of FIG. 8.
Figure 12:
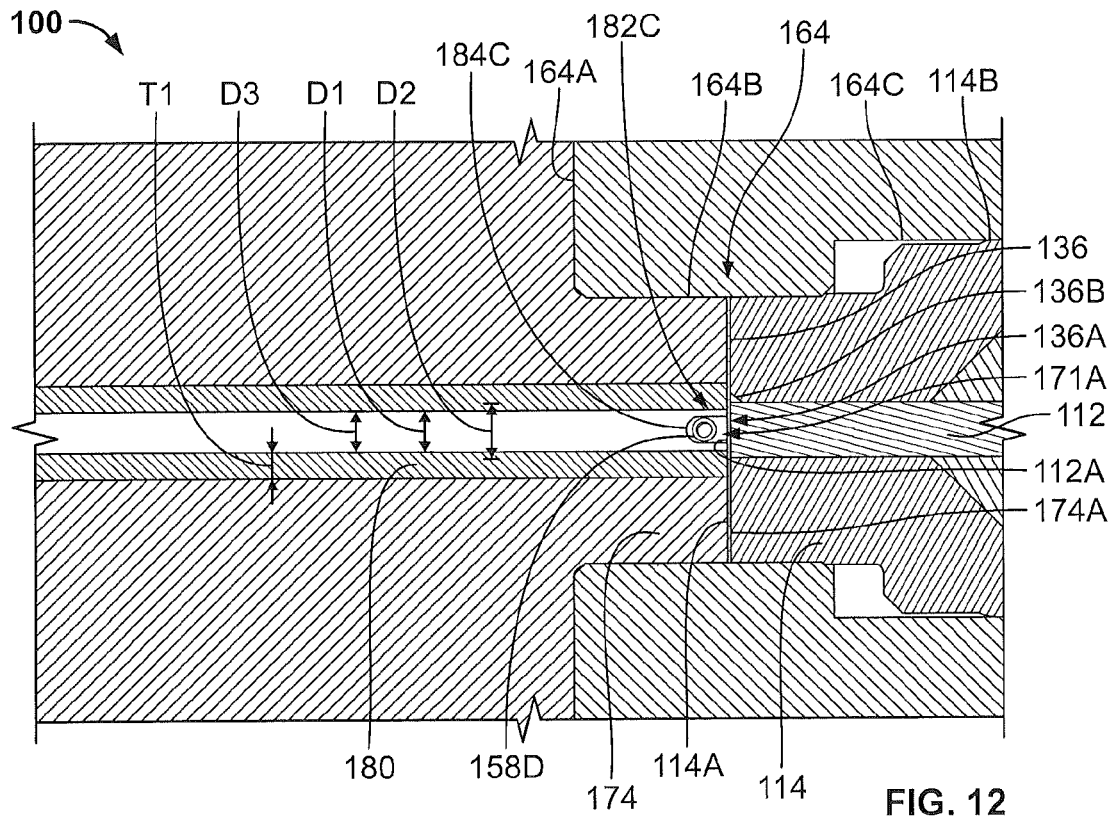
FIG. 12 is an enlarged, cross-sectional view of the flow cell assembly of FIG. 2 taken along the line 12-12 of FIG. 11.
Figure 13:
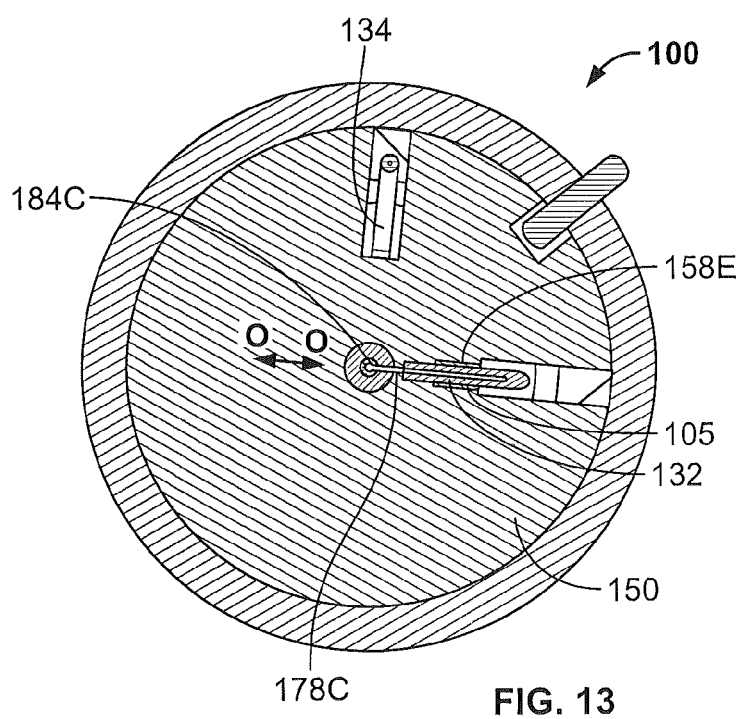
FIG. 13 is a cross-sectional view of the flow cell assembly of FIG. 2 taken along the line 13-13 of FIG. 11.
Figure 14:
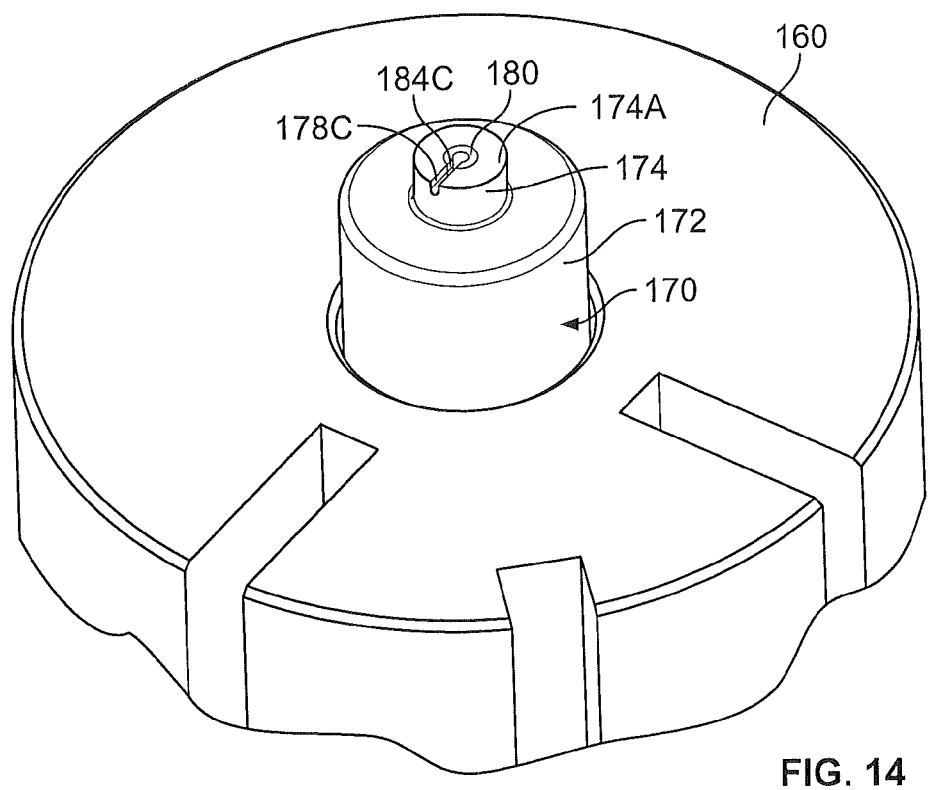
FIG. 14 is a partial perspective view of the flow cell assembly of FIG. 2.
Figure 15:
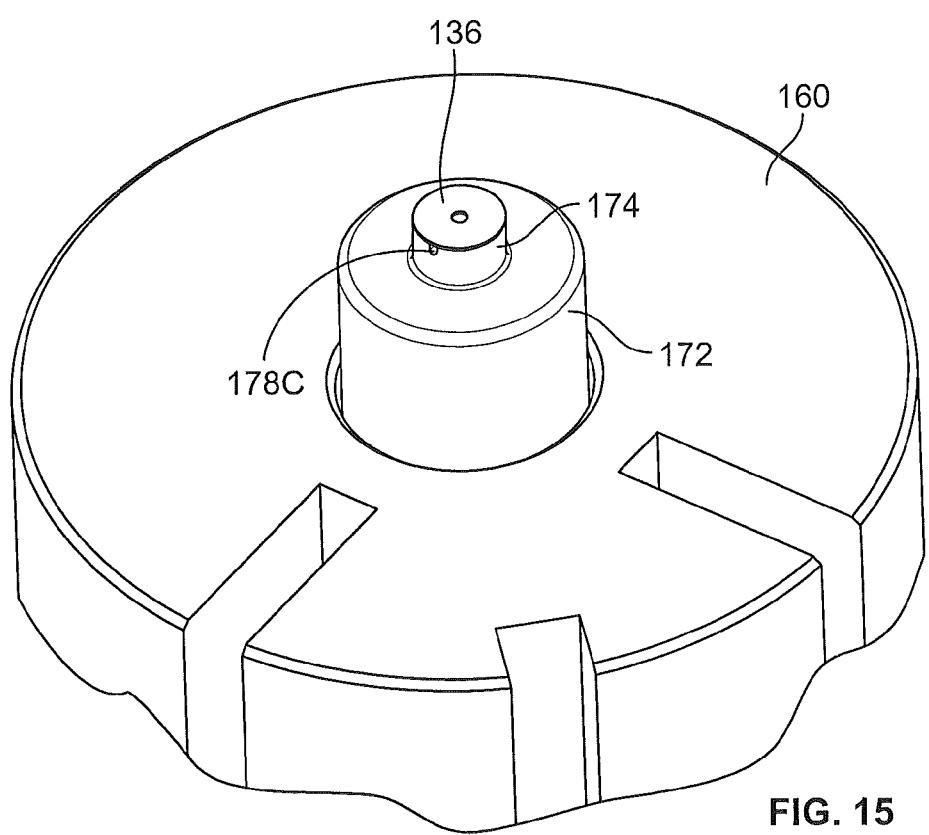
FIG. 15 is a partial perspective view of the flow cell assembly of FIG. 2.

The capillary tubes 132, 134 fluidly couple the flow cell assembly 100 to the liquid sample source 50 and the liquid sample receiver 52, respectively, as discussed in more detail herein. According to some embodiments, the capillary tubes 132, 134 are flexible. In some embodiments, the tubes 132, 134 are formed of fused silica or quartz. According to some embodiments, the tubes 132, 134 are terminated at fluid couplings 104, 106 (FIG. 1) to which the liquid sample source 50 and the liquid sample receiver 52 are fluidly coupled. The tube 132 has an end section 132A and an end opening 132B (FIGS. 4 and 11). The tube 134 has an end section 134A and an end opening 134B (FIGS. 4 and 9).

With reference to FIG. 4, the outer housing 140 may be formed of any suitable material such as metal or a rigid polymer. The outer housing 140 defines a chamber 140A with opposed end openings 140B. An annular base flange 140C is provided at one end and an annular groove 140D is provided at the other end to hold the retainer clip 144. Locator pinholes 140E extend radially through the sidewall of the housing 140.

Figure 5:
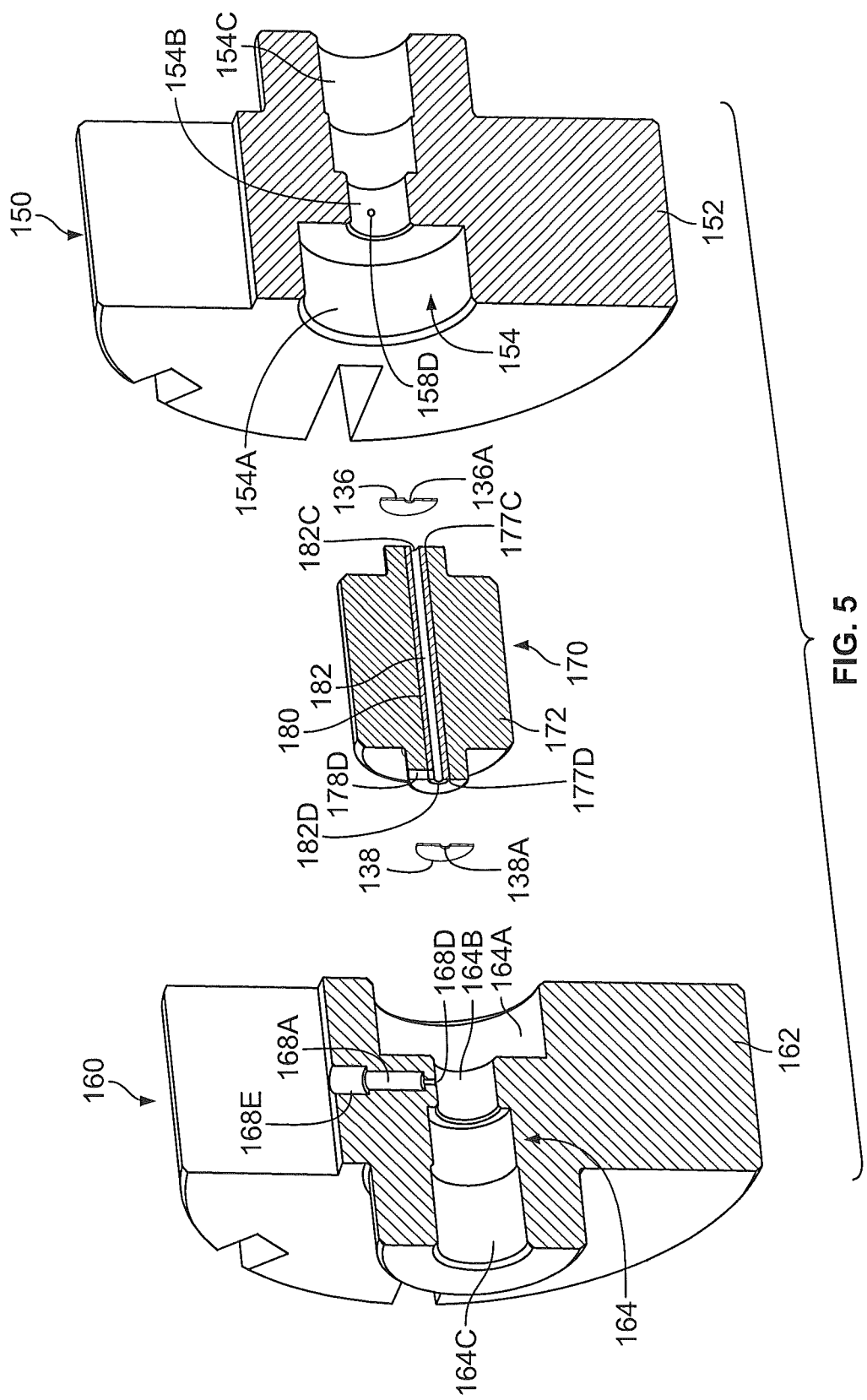
FIG. 5 is an enlarged, exploded, partial, cross-sectional, rear perspective view of the flow cell assembly of FIG. 2.
Figure 6:
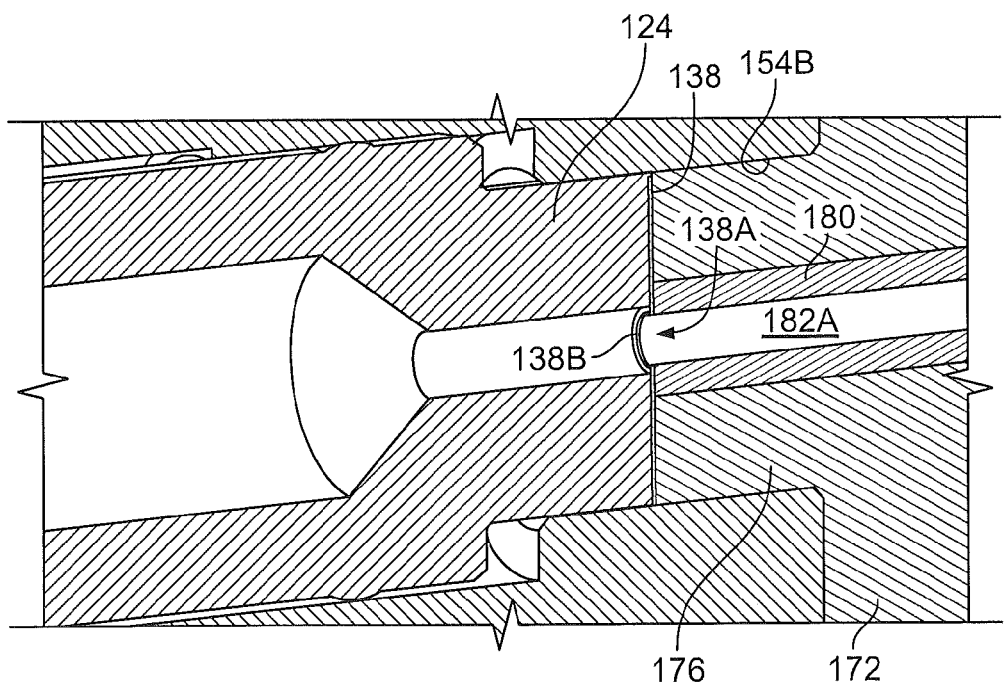
FIG. 6 is a greatly enlarged, fragmentary, partial, cross-sectional view of the flow cell assembly of FIG. 2 wherein a ferrule thereof is shown without its associated optical fiber and epoxy for the purpose of explanation.

With reference to FIG. 5, the entrance joint member 150 includes a body 152 having an axially extending alignment bore 154 defined therein. The bore 154 includes a waveguide receiving bore section 154A, an interface bore section 154B, and a ferrule receiving bore section 154C. Capillary tube channels 156A (FIG. 3) and a locator channel 156B extend axially along the outer periphery of the body 152. A fluidics bore 158 (FIG. 8) extends radially into the body 152 and includes a tube engaging or receiving section 158A (defined by a bore surface 158B) and a fluid conduit section 158C. The bore 158 terminates in an opening or port 158D intersecting the interface bore section 154B. A radially extending waveguide locator pinhole 159 (FIG. 7) is defined in the body 152. According to some embodiments, the joint member 150 is unitary and, in some embodiments, is monolithic.

According to some embodiments, the fluidics bore 158 further includes a counterbore section 158E (FIG. 11) on a side of the tube receiving section 158A opposite the fluid conduit section 158C. As discussed below, the counterbore 158E can contain an epoxy 105 or other adhesive. According to some embodiments, the diameter of the counterbore 158E is in the range of from about 0.3 mm to 0.5 mm greater than the diameter of the tube receiving section 158A.

The exit joint member 160 includes a body 162 having an axially extending alignment bore 164 defined therein. The bore 164 includes a waveguide receiving bore section 164A, an interface bore section 164B, and a ferrule receiving bore section 164C. Capillary tube channels 166A and a locator channel 166B extend axially along the outer periphery of the body 162. A fluidics bore 168 extends radially into the body 162 and includes a tube engaging or receiving section 166A (defined by a bore surface 168B) and a fluid conduit section 168C. The bore 168 terminates in an opening or port 168D intersection the interface bore section 164B. A radially extending waveguide locator pinhole 169 (FIG. 7) is defined in the body 162. According to some embodiments, the joint member 160 is unitary and, in some embodiments, is monolithic.

According to some embodiments, the fluidics bore 168 further includes a counterbore section 168E (FIG. 9) on a side of the tube receiving section 168A opposite the fluid conduit section 168C. As discussed below, the counterbore 168E can contain an epoxy 105 or other adhesive. According to some embodiments, the diameter of the counterbore 168E is in the range of from about 0.3 mm to 0.5 mm greater than the diameter of the tube receiving section 168A.

The joint members 150, 160 may be formed of any suitable biocompatible material(s). According to some embodiments, the joint members 150, 160 are formed of a polymeric material. In some embodiments, the joint members 150, 160 are formed of stainless steel or titanium.

The mask members 136, 138 may be formed of any suitable biocompatible radiation blocking (e.g., light absorbing or reflecting) material such as titanium. Each mask member 136, 138 defines an aperture or opening 136A, 138A and has an annular section 136B, 138B surrounding the opening 136A, 138A.

According to some embodiments, each mask member 136, 138 is formed of a nonresilient material. According to some embodiments, the material of the mask members 136, 138 has a Young's Modulus of at least 14,000 ksi, in some embodiments between about 15,000 ksi and 17,000 ksi, and in some embodiments, at least 16,800 ksi. In some embodiments, the mask members 136, 138 are formed of metal and, in some embodiments, titanium. In some embodiments, the mask members 136, 138 are formed of a ceramic. According to some embodiments, each mask member 136, 138 is a thin disk or wafer having a thickness in the range of from about 0.0005 inch to 0.001 inch.

The flow cell or liquid core waveguide 170 includes a waveguide body 172 and a tubular layer, sleeve or cladding 180 of a light guiding material.

The waveguide body 172 includes an annular entrance flange 174 having an end face 174A and an opposing, coaxial, annular exit flange 176 having an end face 176A. A waveguide passage or bore 177A extends axially through the waveguide body 172, is defined by an inner surface 177B and terminates at opposed end openings 177C and 177D. A radially and axially extending liquid sample feed slot 178C (FIG. 13) is defined in the flange 174 and intersects each of the entrance end opening 177C and the bore 177A. A liquid sample exit slot 178D is defined in the flange 176 and intersects each of the exit end opening 177D and the bore 177A. An axially extending waveguide locator channel 179 is defined in the outer periphery of the body 172.

The cladding layer 180 is tubular and continuous and its outer surface is in intimate contact with the inner surface 177B of the waveguide body 172. In some embodiments, the cladding layer 180 is bonded to or forms a tight interference fit with the inner surface 177B (FIG. 9). The inner surface 182B (FIG. 9) of the cladding layer 180 defines a passage or bore 182A extending axially fully through the waveguide body 172 and terminating at opposed ends 182C, 182D (FIG. 5). A radially and axially extending liquid sample feed slot 184C (FIGS. 12-14) is defined in the cladding layer 180 coincident with the slot 178C and intersects each of the entrance end opening 182C and the bore 182A. A liquid sample exit slot 184D (FIG. 9) is defined in the cladding layer 180 coincident with the slot 178D and intersects each of the exit end opening 182 and the bore 182A. The bore 182A is substantially uniform from end 182C to end 182D. The bore 182A has a longitudinal waveguide bore axis M-M (FIG. 9). The liquid sample feed slot 184C extends radially along a feed slot axis O-O (FIG. 13) transverse to (and, in some embodiments and as illustrated, perpendicular to) the bore axis M-M. The liquid sample exit slot 184D extends radially along an exit slot axis N-N (FIG. 9) transverse to, and in some embodiments perpendicular to, the bore axis M-M.

The waveguide body 172 and the cladding layer 180 may be formed of any suitable materials according to some embodiments, the waveguide body 172 is formed of a polymeric material. In some embodiments, the waveguide body 172 is formed of polyetheretherketone (PEEK).

The cladding layer 180 is formed of a material having a lower refractive index than that of the liquid sample. According to some embodiments, the cladding layer 180 is formed of a fluoropolymer and, in some embodiments, an amorphous fluoropolymer. According to some embodiments, the cladding layer 180 is formed of an amorphous copolymer of perfluora-2,2-dimethyl-1,3-dioxole and tetrafluoroethylene, an example of which is sold by E.I. du Pont de Nemours (commonly referred to as DuPont) under the trademark Teflon AF 2400™.

According to some embodiments, the cladding layer 180 has a thickness T1 (FIG. 12) in the range of from about 0.005 to 0.010 inch and, in some embodiments, from about 0.10 to 0.020 inch. According to some embodiments, the cladding layer 180 is substantially free of any internal microbends or kinks. According to some embodiments, the inner diameter D3 of the cladding layer 180 is in the range of from about 0.007 to 0.010 inch and, in some embodiments, from 0.010 to 0.015 inch.

The flow cell assembly 100 may be constructed as follows. The locator pins 146 are press fit into the locator pinholes 140E so that they protrude into the chamber 140A. The waveguide locator pins 148 are press fit through the holes 159, 169 such that they project into the waveguide receiving bore sections 154A, 164A.

The end section 132A of the feed capillary tube 132 is inserted into the tube receiving bore section 158A of the entrance joint member 150 until the tube 132 bottoms out with the end opening 132B mated with the fluid conduit bore 158C.

According to some embodiments, the inner diameter of the bore section 158A is smaller than the outer diameter of the tube section 132A so that the bore surface 158B forms an interference fit with the tube section 132A. In some embodiments, the inner diameter of the bore section 159A is in the range of from about 0.0005 to 0.001 inch less than the outer diameter of the tube section 132A. According to some embodiments, the interference fit between the inner surface 158B and the tube section 132A forms a fluid tight seal under all intended operating conditions (e.g., pressures and temperatures).

According to some embodiments, an adhesive 105 is applied to a section of the capillary tube 132 proximate the tube section 132A prior to inserting the tube section 132A into the receiving bore section 158A. The adhesive 105 is received in the counterbore 158E and adheres the capillary tube 132 in the bore 158. In some embodiments, the adhesive is an epoxy. In some embodiments, the tube section 132A is secured in the bore 158 by brazing.

Similarly, the end section 134A of the exit capillary tube 134 is seated in the tube receiving bore section 168A of the exit joint member 160 in the same manner as described above for the tube 132 and the joint member 150. According to some embodiments, the tube section 134A forms an interference fit with the bore inner surface 168B to provide a fluid tight seal under all intended operating conditions. According to some embodiments, an adhesive 105 is applied to a section of the capillary tube 134 proximate the tube section 134A prior to inserting the tube section 134A into the receiving bore section 168A. The adhesive 105 is received in the counterbore 168E and adheres the capillary tube 134 in the bore 168. In some embodiments, the adhesive is an epoxy. In some embodiments, the capillary tube 134 is secured in the bore 168 by brazing.

The components of the flow cell assembly 100 are then stacked in the outer housing 140. The spring 142 is placed on the flange 140C. The exit joint member 160 is placed on the spring 142 such that the lower locator pin 146 is received in the channel 169. The exit flange 176 of the waveguide 170 is inserted into the bore section 164A such that the lower locator pin 148 is received in the locator channel 179. The entrance joint member 150 is placed on the waveguide 170 such that the entrance flange 174 of the waveguide 170 is received in the bore section 154A, the upper waveguide locator pin 148 is inserted in the locator channel 179, and the upper locator pin 146 is received in the locator channel 159. The capillary tubes 132, 134 are routed through the channels 156A, 166A as illustrated. The several components are secured in place by installing the retainer clip 144 in the groove 140D. According to some embodiments, the spring 142 is maintained by the clip 144 in an elastically compressed condition so that the joint members 150, 160 and the waveguide 170 are tightly and persistently axially compressed against one another at their abutting surfaces. A flow cell module 101 is thereby constructed.

The mask members 136, 138 and connectorized fibers 110, 120 may then be installed on the foregoing subassembly or flow cell module 101. The mask member 136 is placed in the interface bore section 154B on the end face 174A of the waveguide 170. The mask member 136 is centered by the bore section 154B so that the mask opening 136A is substantially concentric with the waveguide bore 182A. The ferrule 114 is then inserted into the bore 154 until the ferrule end face 114A abuts the mask 136. The bore 154 likewise substantially concentrically aligns the ferrule 114 and thereby the fiber 112, with the waveguide bore 182A. The mask member 138 and the ferrule 124 are likewise installed in the bore 164 of the exit joint member 160. The ferrules 114, 124 may be secured in the respective bore sections 154C, 164C by interference fit, epoxy, and/or interlock between the ribs 114B, 124B and cooperating features in the bores 154, 164.

The flow cell assembly 100, now assembled, can be connected to the light source 20, the detector 30, the liquid sample source 50 and the liquid sample receiver 52 via the connectorized fiber 110, the connectorized fiber 120, the feed tube 132 and the exit tube 134, respectively.

In use, a flow of the liquid sample is pumped or otherwise driven, sequentially, from the liquid sample source 50, through the feed tube 132, radially through the fluid conduit bore 158C, radially through the feed port 158D, radially through a conduit 171A (defined collectively by the feed slots 178C, 184C, the fiber end face 112A and the inner face of the mask 136), axially through the waveguide bore 182A, radially through a conduit 171B (defined collectively by the exit slots 178D, 184D, the fiber end face 122A, and the inner face of the mask 138), radially through the exit port 168D, radially through the conduit bore 168C, through the exit tube 134, and to the liquid sample receiver 52.

Simultaneously, a beam of optical energy (i.e. light or other radiation) emitted from the source 20 is transmitted, in sequence, into the input fiber 112 through the end face 112A, through the fiber 112, into the bore 182A, through the fiber end face 112B, through the liquid sample in the bore 182A into the exit fiber 122 through the end face 122A, and through the fiber 122 to the input of the detector 30. The liquid sample in the bore 182A serves as an optical core and the cladding layer 180 serves as an optical cladding providing total internal reflection. The waveguide 170 has an illuminated path length LP (i.e., the axial length of the column of liquid sample illuminated in the bore 182A) extending from the fiber end face 112A to the fiber end face 122A.

The mask members 136, 138 block light from entering the waveguide body 172 from the fiber 112 and from entering the fiber 124 from the waveguide body 172. In this manner, the flow cell assembly 100 can prevent stray light from being transmitted to the detector 30 through the waveguide body 172 and thereby bypassing the liquid sample in the bore 182A. According to some embodiments, the inner diameter D1 of each mask member 136, 138 is less than the outer diameter D2 of the adjacent optical fiber 112, 122 and substantially the same as the inner diameter D3 of the cladding layer 180 so that an annular inner section 136B, 138B of the mask member 136, 138 overlaps the fiber end face 112A, 122A. In some embodiments, the inner diameter D1 is between about zero and 0.001 inch less than the outer diameter D2.

In an exemplary embodiment, the detector 30 is a PDA spectrometer including a photodiode array and a grating to divide an incident light beam into prescribed wave lengths (or ranges of wave lengths) and project the different wave lengths onto different respective photodiodes of the PDA. The liquid sample is axially illuminated by the source beam from the source 20. The illuminated liquid sample will absorb and thereby attenuate the light at different wave lengths in accordance with its composition. The voltage of each photodiode will be reduced in proportion to the reduction of its corresponding wave length in the light beam exiting the liquid sample through the optical fiber 122.

Liquid sample analyzers and flow cell assemblies according to embodiments of the technology can provide a number of benefits and advantages. Sensing devices such as PDA spectrometers typically require low flow cell dispersion and fast data rates and high light flux. It is desirable to provide a flow cell assembly that is compact and that can be flexibly integrated into a PDA spectrometer system.

The cladding sleeve 180, particularly when formed of a material as discussed hereinabove and providing total internal reflection, allows for a smaller volume flow cell without loss of optical signal, thereby increasing output resolution.

The mask members 136, 138 can reduce or eliminate transmission of stray light to the detector 30, thereby reducing noise or distortion in the optical signal.

The use of bendable fibers 112, 122 for light beam entry and exit allows for increased flexibility in system packaging. The flow cell module 101 can be placed in a wide range of locations and orientations. For example, the terminations 116 and 126 can be relatively positioned at a right angle to one another.

The flow cell assembly 100 is adaptable to multiple path lengths. The illuminated path length LP can be varied by simply providing a waveguide 170 having a different length and an outer housing 140 having a corresponding different length. Because the fluid connections are provided in the independent joint members 150, 160, the liquid sample inlet port and the liquid sample exit port can be spaced apart to accommodate a waveguide 170 of any desired length. For example, FIGS. 16 and 17 show an alternative flow cell assembly 200 wherein the housing 140 has been replaced with a longer housing 240 and the waveguide 170 has been replaced with a longer waveguide 270 having a correspondingly longer illuminated path length LP2. According to some embodiments, flow cell assemblies as disclosed herein are provided having a path length in the range of from about 0.1 cm (e.g., 0.1 μl) to about 10 cm (e.g., 10 μl).

The design of the flow cell assembly 100 can enable higher photon flux combined with lower light dispersion. Dispersion is minimized or reduced by the integration of the fluidics into the waveguide 170. The flow cell assembly 100 can use very low volume capillary tubing for the feed tube 132 and the exit tube 134. The flow cell assembly 100 can be configured with very low dead volume.

The flow cell assembly 100 can be constructed more simply and with fewer parts than some known designs. The design facilitates ease of assembly and more robust and reliable fluidic sealing than some existing designs.

The component geometry enables inherent precision alignment, which can reduce dead volume and increase optical throughput. More particularly, the geometries of the ferrules 114, 124, the waveguide flanges 174, 176, the masks 136, 138, and the joint member bores 154, 164 are relatively arranged and configured to ensure radial positioning of and coaxial alignment between the fiber end faces 112A, 122A, the mask holes 136A, 138A, and the waveguide bore openings 182C, 182D (and thereby the bore 182A). Likewise, axial alignment can be ensured between the joint member feed port 158D and the waveguide feed slot 178C, and between the joint member exit port 168D and the waveguide exit slot 178D. Moreover, these geometries can, in combination with axial loading of the spring 142, ensure that the components are tightly abutted at their interfaces to provide reliable and robust fluid seals.

The locator pins 146, 148 and the locator channels 156B, 166B, 179 can insure proper rotational alignment between the joint member feed port 158D and the waveguide feed slot 178C and between the joint member exit port 168D and the waveguide exit slot 178D. The interference fit "T" joints between the joint members 150, 160 and the tubes 132, 134 can ensure a robust seal that is at less risk of being compromised by relative shifts or movements of the components of the flow cell assembly 100.

According to some embodiments, the flow cell assembly 100 is capable of withstanding back pressures up to at least about 1500 psi without leakage.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A flow cell assembly for use in a liquid sample analyzer, the liquid sample analyzer including a radiation source, a sensing device and a liquid sample source to supply a liquid sample, the flow cell assembly comprising:
   a joint member including an axially extending alignment bore, the alignment bore including a waveguide receiving bore section and an optical fiber termination receiving bore section;
   a liquid core waveguide mounted in the waveguide receiving bore section, the liquid core waveguide defining a waveguide bore; and
   an optical fiber assembly including an optical fiber and an optical fiber termination mounted on an end of the optical fiber, wherein the end of the optical fiber and the optical fiber termination are mounted in the optical fiber termination receiving bore section, the optical fiber having an exposed optical fiber end face adjacent the optical fiber termination;
   wherein the alignment bore radially aligns the liquid core waveguide with the optical fiber termination and thereby radially aligns the optical fiber end face with the waveguide bore; and
   wherein the optical fiber is operative to transmit radiation from the radiation source to the waveguide bore, which radiation is transmitted through the waveguide bore and the liquid sample therein to the sensing device; and wherein:
the alignment bore further includes an interface bore section axially interposed between the waveguide receiving bore section and the optical fiber termination receiving bore section;
an end portion of the liquid core waveguide and an opposing end portion of the optical fiber termination are each disposed in the interface bore section; and
the interface bore section radially aligns the end portion of the liquid core waveguide with the opposing end portion of the optical fiber termination and thereby radially aligns the optical fiber end face with the waveguide bore.

2. The flow cell assembly of claim 1 wherein:
the joint member is unitary and includes a feed tube receiving bore;
the flow cell assembly includes a liquid sample feed tube mounted in the feed tube receiving bore such that the liquid sample feed tube is in fluid communication with the waveguide bore to fluidly connect the liquid sample source to the waveguide bore.

3. The flow cell assembly of claim 2 wherein:
the waveguide bore defines a longitudinally extending waveguide bore axis; and
the feed tube receiving bore extends radially with respect to the waveguide bore axis.

4. The flow cell assembly of claim 2 wherein:
the feed tube receiving bore includes a feed tube engaging section and a counterbore section;
the feed tube engaging section forms as interference fit with the liquid sample feed tube; and
the flow cell assembly further includes an adhesive in the counterbore section bonding the liquid sample feed tube to the counterbore section.

5. The flow cell assembly of claim 2 wherein the liquid core waveguide includes:
an outer waveguide body defining a waveguide body bore; and
a cladding layer mounted in the waveguide body bore and defining the waveguide bore;
wherein the cladding layer is formed of a material having a lower refractive index than the liquid sample.

6. The flow cell assembly of claim 2 including:
an exit joint member including a waveguide receiving bore and an exit tube receiving bore, wherein the liquid core waveguide is also mounted in the waveguide receiving bore of the exit joint member;
a liquid sample exit tube mounted in the exit tube receiving bore such that the liquid sample exit tube is in fluid communication with the waveguide bore to fluidly connect the waveguide bore to a liquid sample receiver; and
an output optical fiber mounted in the exit joint member to transmit radiation from the waveguide bore to the sensing device.

7. The flow cell assembly of claim 1 including a mask member disposed in the interface bore section between the liquid core waveguide and the optical fiber termination, the mask member defining an aperture to permit transmission of light from the optical fiber end face through the aperture into the waveguide bore.

8. The flow cell assembly of claim 1 wherein the liquid core waveguide is fluidly sealed in the alignment bore.

9. The flow cell assembly of claim 1 wherein the interface bore section coaxially aligns the optical fiber and the waveguide bore.

10. The flow cell assembly of claim 1 wherein the optical fiber termination is a ferrule.

11. The flow cell assembly of claim 10 wherein:
the ferrule is secured to the end of the optical fiber by adhesive; and
the ferrule has an end face and the end face of the optical fiber is substantially flush with the end face of the ferrule.

12. The flow cell assembly of claim 1 wherein:
a liquid core waveguide includes a cladding layer formed of a material having a lower refractive index than the liquid sample, wherein the cladding layer defines:
the waveguide bore, wherein the waveguide bore extends axially and has a bore input end and a bore output end;
an input opening at the bore input end; and
a liquid sample feed slot extending radially through the cladding layer and intersecting each of the waveguide bore and the input opening;
wherein the flow cell assembly is configured to feed a flow of the liquid sample into the waveguide bore through the liquid sample feed slot.

13. The flow cell assembly of claim 12 wherein:
the cladding layer defines an exit end opening at the output bore end;
the cladding layer further defines a liquid sample exit slot extending radially through the cladding layer and intersecting each of the waveguide bore and the output opening; and
the flow cell assembly is configured to remove the flow of the liquid sample from the waveguide bore through the liquid sample exit slot.

14. The flow cell assembly of claim 13 wherein the cladding layer is a tubular sleeve terminating at the input and output bore ends and the waveguide bore has a substantially uniform diameter from the first bore end to the second bore end.

15. The flow cell assembly of claim 1 wherein the end portion of the liquid core waveguide and the opposing end portion of the optical fiber termination each engage the joint member in the interface bore section to positively concentrically align the optical fiber end face with the waveguide bore.

16. The flow cell assembly of claim 1 wherein a diameter of the interface bore section is less than a diameter of the waveguide receiving bore section and a diameter of the optical fiber termination receiving bore section.

17. The flow cell assembly of claim 1 wherein the end face of the optical fiber is located in the interface bore section.

18. The flow cell assembly of claim 1 wherein the optical fiber termination is secured to the end of the optical fiber by adhesive.

19. The flow cell assembly of claim 1 wherein the optical fiber termination has an end face and the end face of the optical fiber is substantially flush with the end face of the optical fiber termination.

20. The flow cell assembly of claim 1 wherein the end face of the optical fiber is located adjacent and outside of the waveguide bore.

21. The flow cell assembly of claim 20 wherein the end face of the optical fiber defines a portion of a flow path of the liquid sample entering or exiting the waveguide bore.

22. The flow cell assembly of claim 1 wherein the optical fiber termination is secured in the optical fiber termination receiving bore section by at least one of an interference fit, epoxy and an interlock between cooperating interlock features on the optical fiber termination and the joint member in the optical fiber termination receiving bore section.

23. The flow cell assembly of claim 1 including a spring biasing the joint member and the liquid core waveguide against one another.

* * * * *